United States Patent [19]

Spindler et al.

[11] Patent Number: 5,100,791
[45] Date of Patent: Mar. 31, 1992

[54] SIMULTANEOUS SACCHARIFICATION AND FERMENTATION (SSF) USING CELLOBIOSE FERMENTING YEAST *BRETTANOMYCES CUSTERSII*

[75] Inventors: Diane D. Spindler, Indian Hills; Karel Grohmann, Littleton; Charles E. Wyman, Lakewood, all of Colo.

[73] Assignee: The United States of America as represented by the United States Department of Energy, Washington, D.C.

[21] Appl. No.: 642,268

[22] Filed: Jan. 16, 1991

[51] Int. Cl.⁵ .......................... C12P 7/08; C12P 7/06; C12P 7/10; C12R 1/645g300101
[52] U.S. Cl. .................... 435/163; 435/42; 435/95; 435/96; 435/98; 435/161; 435/162; 435/165; 435/911
[58] Field of Search ............. 435/161, 42, 162, 163, 435/165, 911, 96, 95, 98

[56] References Cited

U.S. PATENT DOCUMENTS

| | | | |
|---|---|---|---|
| 4,288,550 | 9/1981 | Ishida et al. | 435/161 |
| 4,359,534 | 11/1982 | Kurtzman et al. | 435/161 |
| 4,368,268 | 1/1983 | Gong | 435/161 |
| 4,385,117 | 5/1983 | Ljungdahl et al. | 435/172.1 |
| 4,414,329 | 11/1983 | Wegner | 435/255 |
| 4,464,471 | 8/1984 | Armentrout et al. | 435/161 |
| 4,472,501 | 9/1984 | Takasawa et al. | 435/165 |
| 4,511,656 | 4/1985 | Gong | 435/161 |
| 4,567,145 | 1/1986 | Faber et al. | 435/161 |
| 4,612,286 | 9/1986 | Sherman et al. | 435/163 |
| 4,701,414 | 10/1987 | Van Dijken et al. | 435/163 |
| 4,840,903 | 6/1989 | Wu | 435/165 |

OTHER PUBLICATIONS

JPOABS 61-81783, Apr. 25, 1986, Yabuki, J59203090.
JPOABS 61-31080, Feb. 13, 1986, Tsumura et al., J59-153209.
JPOABS 62-96090, May 2, 1987, Tsumura et al., J61-249559.
R. Dekker, Biotechnology Letters, vol. 4, No. 7, pp. 411–416, 1982.
R. Maleszka et al., Biotechnology Letters, vol. 4, No. 2, pp. 133–136, 1982.

*Primary Examiner*—Herbert J. Lilling
*Attorney, Agent, or Firm*—Kenneth Richardson; James W. Weinberger; William R. Moser

[57] ABSTRACT

A process for producing ethanol from plant biomass includes forming a substrate from the biomass with the substrate including hydrolysates of cellulose and hemicellulose. A species of the yeast *Brettanomyces custersii* (CBS 5512), which has the ability to ferment both cellobiose and glucose to ethanol, is then selected and isolated. The substrate is inoculated with this yeast, and the inoculated substrate is then fermented under conditions favorable for cell viability and conversion of hydrolysates to ethanol.

18 Claims, 2 Drawing Sheets

SIMULTANEOUS SACCHARIFICATION AND FERMENTATION (SSF) USING CELLOBIOSE FERMENTING YEAST *BRETTANOMYCES CUSTERSII*

CONTRACTUAL ORIGIN OF THE INVENTION

The United States Government has rights in this invention under Contract No. DE-AC02-83CH10093 between the U.S. Department of Energy and the Solar Energy Research Institute, a Division of Midwest Research Institute.

BACKGROUND OF THE INVENTION

1. Field of the Invention

The invention relates to the production of ethanol and more particularly, to a method for the production of ethanol in high yields from cellobiose fermenting yeast *Brettanomyces custersii* in a simultaneous saccharification and fermentation process employing cellulosic materials as a substrate.

2. Description of the Prior Art

In the past, the production of ethanol has been procured by a procedure comprising the steps of reacting cellulase upon cellulose as the substrate to enzymatically saccharify the cellulose to glucose, and then separately causing the resultant glucose to be reacted upon by an ethanol-producing microorganism to produce ethanol. However, using this conventional method, the conversion of cellulose to glucose by a cellulase is low and, as a consequence, large amounts of unconverted cellulosic residue are obtained. Accordingly, low yields of ethanol are obtained by subjecting the saccharified liquid to fermentation.

Nevertheless, ethanol is of great interest to a wide variety of industries due to past and potential future energy crisis situations, and the conversion of these cellulose materials to useful fuels such as ethanol is of special interest.

Cellulose and hemicellulose are the two most abundant and renewable raw organic compounds in the world and together they compose about 70 percent of the entire world's plant biomass on a dry weight basis. These raw materials are widely available in the waste from agricultural, forest, vegetable, and food process sources and the efficient conversion of these wastes to useful products such as ethanol, would help reduce disposal problems as well as provide an abundant and cheap source of fuel. Other cellulose containing biomass can be grown specifically to provide a feedstock for ethanol manufacture and to support wide scale ethanol production for use as a fuel.

More specifically, plant biomass generally contains from 40-50 percent cellulose and 30-40 percent hemicellulose, and a balance of lignin. If a process for converting the bulk of the cellulose and hemicellulose to ethanol in high yields could be devised, this process could provide an almost unlimited supply of liquid fuel for transportation uses.

Cellulose is readily broken down to its glucose and cellobiose hydrolysate products by acid hydrolysis or enzymatic hydrolysis treatment. While glucose is readily fermentable by many microorganisms to ethanol, cellobiose has proven difficult, at best, to convert to ethanol. Even then, it is convertible to ethanol only in very low yields or low concentrations. (R. Dekker, Biotechnology Letters, Volume 4, No. 7, Pages 411–416, 1982; R. Maleszka, et al., Biotechnology Letters, Volume 4, No. 2, pp. 133-136, 1982).

Hemicellulose is likewise readily and easily converted to its various hydrolysate products by mild acid hydrolysis or enzymatic hydrolysis treatment and the resultant products include various pentoses (xylose and arabinose being the main derivatives), hexoses (mannose and galactose), and sugar acids. By far, D-xylose is the major sugar in hemicellulose hydrolysate and constitutes approximately 60-80 percent of the total hydrolysates produced therefrom.

A variety of processes which use different yeasts to ferment xylose to ethanol have been investigated and disclosed in the literature. A prime motivating force behind these investigations is that the fermentation of 5-carbon sugars derived from hemicellulose is extremely important in order to fully utilize biomass material in producing ethanol. Examples of such prior art techniques include U.S. Pat. Nos. 4,511,656, 4,368,268, 4,359,534, and 4,477,569. However, these processes do not convert D-xylose to ethanol in sufficient yields and at sufficiently high rates to be efficient and cost effective.

U.S. Pat. No. 4,385,117 pertains to a process for continuously producing ethanol such that a substrate can be added to a fermentation and the ethanol can be removed therefrom during a fermentation comprising, subjecting an aqueous nutrient medium containing the substrate at a substrate concentration in the fermentation medium greater than one percent (w/v) wherein the substrate is starch, pectin, monosaccharides and disaccharides, under anaerobic and thermophilic conditions to the fermentation action of a derivative of the microorganism *Thermoanaerobacter ethanolicus*; however, this patent is directed to a thermophilic rather than a mesophilic microorganism which is reported on substrates greater than one percent, and where it is apparent that a sharp decrease in ethanol tolerance on starch concentrations above one percent exist, and this of course is a very low substrate loading in a saccharification and fermentation process.

U.S. Pat. No. 4,464,471 is directed to a recombinant DNA plasmid comprising a cloning vector having covalently bound thereto a DNA insert coding for the production of beta-glucosidase wherein the DNA insert coding for the production of beta-glucosidase is isolated from *Esherichia adecarboxylata*; but this patent is directed to a genetically engineered microorganism via plasmid coding, and this is not a natural organism and it has not been demonstrated in simultaneous saccharification fermentation processes.

U.S. Pat. No. 4,472,501 pertains to a process for producing ethanol comprising culturing a microorganism from the group of microorganisms having the identifying characteristics of *Kluyveromyces cellobiovorus* NRRL Y-12509 and a microorganism having the identifying characteristics of *Kloeckera apiculata* NRRL Y-12510 and which is capable of producing ethanol and assimilating at least one carbon source selected from xylose and cellobiose, in a medium containing an assimilable source of at least one of said xylose and cellobiose until a recoverable amount of ethanol is produced in the culture liquor and thereafter recovering said ethanol therefrom; however, the microorganisms are different from those of the invention and said microorganisms are compared in their performance to a glucose fermentor (*Saccharomyces cerevisiae*) albeit one of their organisms demonstrates a low ethanol yield on crystalline cellulose and the others were fermented on glucose, xylose and/or cellobiose.

In U.S. Pat. No. 4,840,903, there is disclosed a process for producing ethanol from plant biomass by forming a substrate from said biomass, wherein the substrate includes hydrolysates of cellulose and hemicellulose, after which a species of the fungus Paecilomyces, which has the ability to ferment both cellobiose and xylose to ethanol, is then selected and isolated. The substrate is inoculated with said fungus and the inoculated substrate is fermented under conditions favorable for cell viability and conversion of hydrolysates to ethanol, and the ethanol is recovered from the fermented substrate; however, the conversion of cellobiose and xylose to ethanol is by the mechanism of a fungus, and not by a yeast, and the yields and rates of ethanol are not sufficient for the simultaneous saccharification process to be economically feasible.

SUMMARY OF THE INVENTION

It is an object of the invention to provide for improved rates and yields of ethanol in a simultaneous saccharification fermentation process, and towards these ends, this invention achieves these results by incorporating a yeast that can ferment not only glucose, but cellobiose as well, because it produces its own beta-glucosidase enzyme.

A further object of this invention is to provide a yeast that will ferment cellobiose in a simultaneous saccharification and fermentation process without the need for large and costly supplementation of the process with beta-glucosidase enzyme in order to avoid low ethanol rates and yields.

A yet further object of the invention is to provide cellobiose fermentating yeast strains for use in simultaneous saccharification and fermentation processes that is neither characterized by a low ethanol tolerance nor a low ethanol production rate.

A still further object of the invention is to provide a yeast that can ferment not only glucose, but cellobiose as well, because it produces its own beta-glucosidase enzyme.

The present invention process accomplishes the foregoing objects by using *Brettanomyces custersii* (CBS 5512) as a cellobiose fermentor in a simultaneous saccharification fermentation process, wherein said yeast displays a high ethanol tolerance (namely, about 94 grams per liter) and a high temperature tolerance range (30° C.-37° C.) and gives high ethanol conversion rates and yields.

BRIEF DESCRIPTION OF THE DRAWINGS

The accompanying drawings, which are incorporated in and form a part of the the specification, illustrate preferred embodiments of the present invention, and together with the description, serve to explain the principles of the invention.

IN THE DRAWINGS

Figure 1:
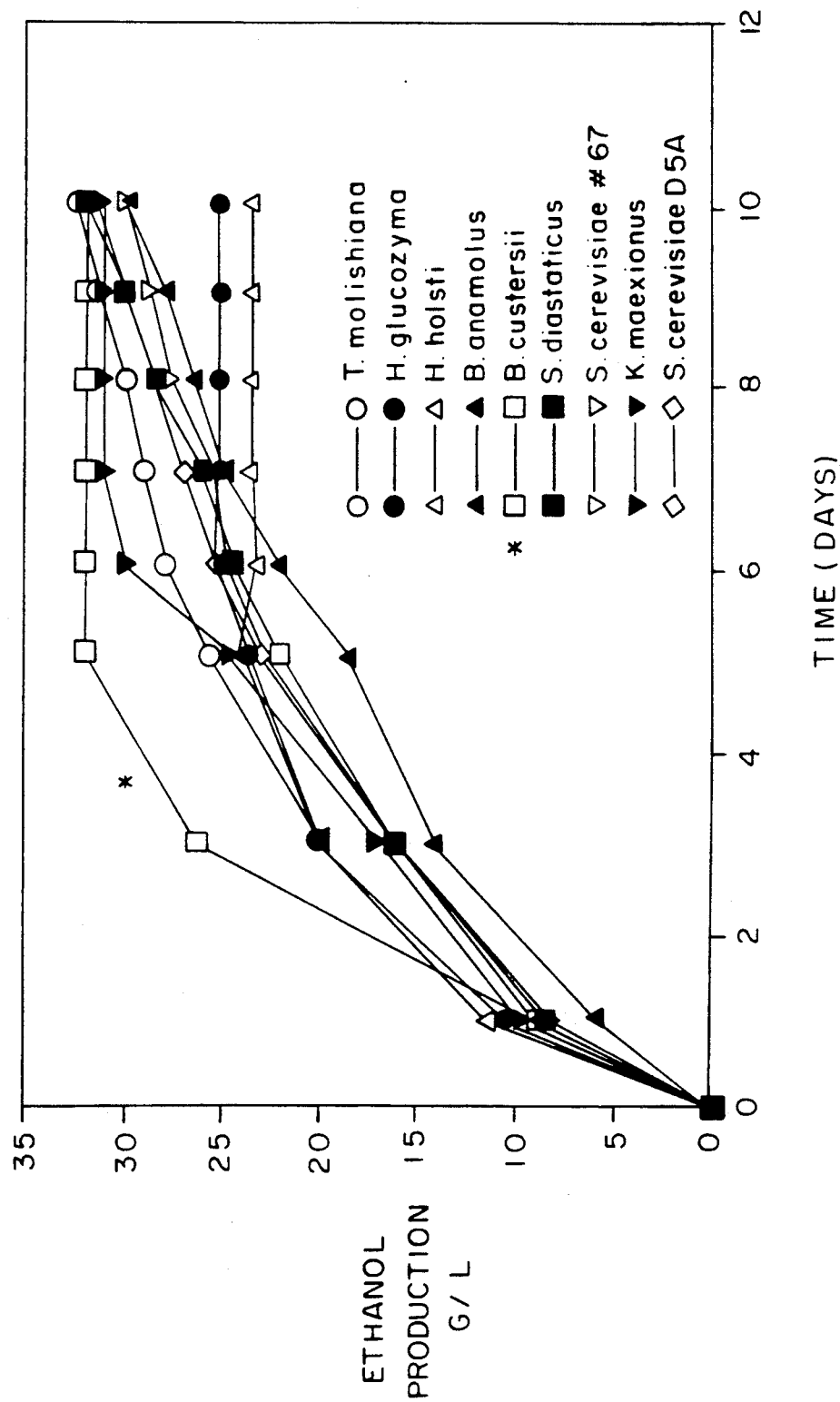

FIG. 1 is a comparison graph depicting ethanol production yields and rates using the cellobiose fermenting yeast *Brettanomyces custersii* compared to other yeast strains in a simultaneous saccharification and fermentation process employing cellulose and cellulase enzyme.

Figure 2:
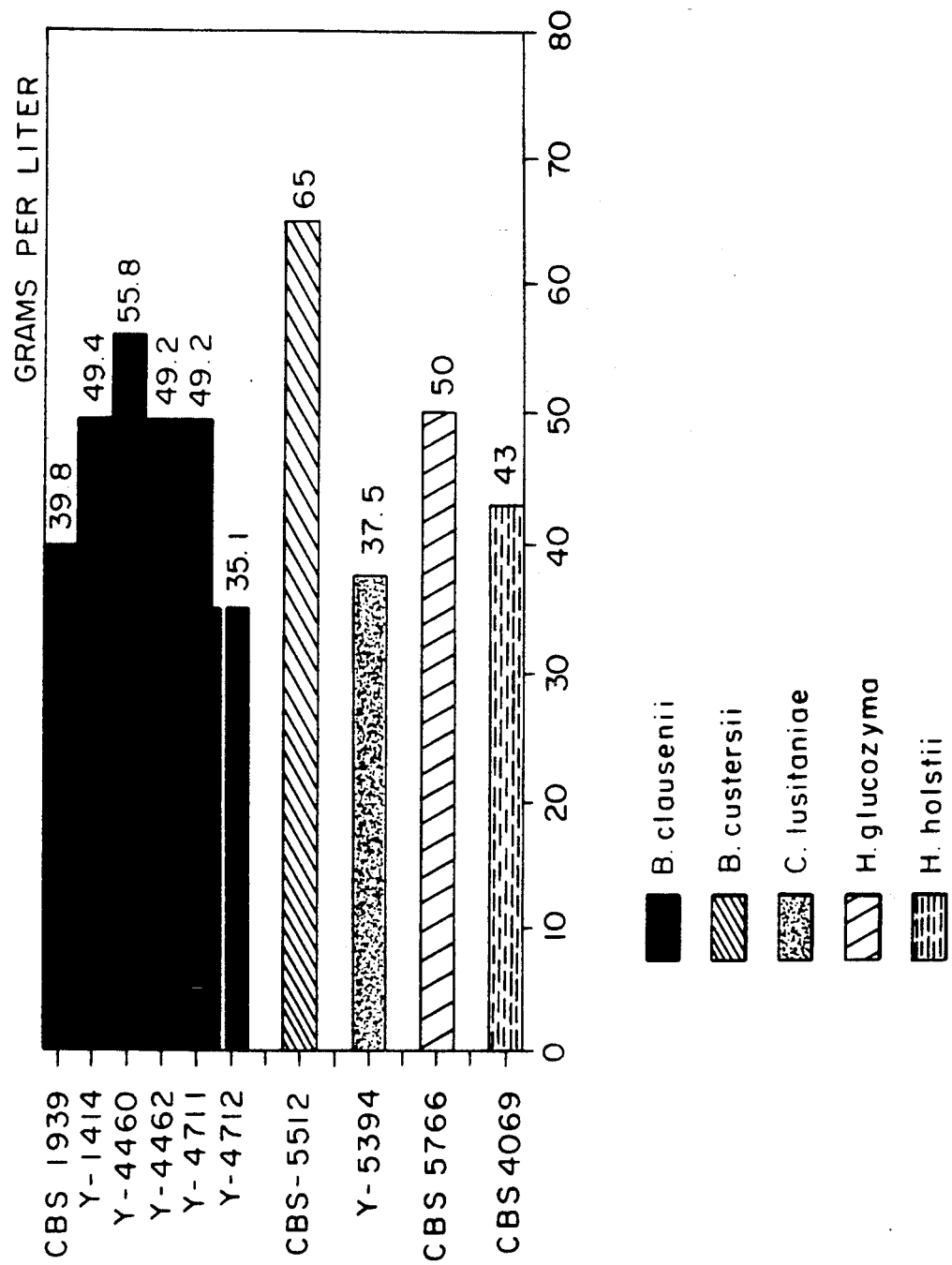

FIG. 2 is a graph comparing ethanol production from 15% cellobiose by *B. custersii* yeast screened at 37° C. compared to other fermenting yeast under the same conditions.

DETAILED DESCRIPTION OF THE INVENTION

In a simultaneous saccharification fermentation process, saccharification involves the breakdown of cellulose into simpler sugars by a cellulase enzyme. One such sugar is cellobiose, a sugar comprised of two glucose molecules that is subsequently broken down into glucose. The cellulase enzyme will typically have an insufficient amount of beta-glucosidase, which is the part of the cellulase enzyme that can breakdown cellobiose into glucose. Cellobiose inhibits the endo- and exo-glucanase enzymes, and this retards the overall ethanol production rate and yield in a simultaneous saccharification fermentation process.

There exist, commercially available industrial yeast strains that will ferment glucose and maltose, but not cellobiose, and this occasions the need for large supplementation of the simultaneous saccharification fermentation process with beta-glucosidase enzymes in order to avoid low ethanol production rates and low ethanol yields, and this supplementation process is very costly. On the other hand, where cellobiose fermenting yeast strains have been found, they generally have a low ethanol tolerance and a low ethanol production rate.

The yeast strain *Brettanomyces custersii* (CBS 5512) has been found to ferment cellobiose very well at about 37° C. when used in a simultaneous saccharification fermentation process, and provides both a faster rate of ethanol production and a higher ethanol yield over other known cellobiose fermenting yeast.

The essence and importance of the present invention is that this process is capable of producing high yields and concentrations of ethanol from a wide variety of six carbon sugars derived from cellulose and hemicellulose. More particularly, the present invention ferments disaccharides such as sucrose, maltose, lactose and cellobiose (but excluding melibiose and trehalose), polysaccharides such as starch and hexoses such as glucose, fructose, sorbose, mannose and galatose. Thus, high yields of ethanol can be produced from the bulk of the products of cellulose and hemicellulose hydrolysis as well as some of the sugars derived therefrom, thereby providing a highly economic process for producing ethanol.

In particular, the present invention is a process using the yeast strain *Brettanomyces custersii* to produce ethanol by fermentation. The solution to be fermented may include a mixture of the cellulose hydrolysates D-cellobiose and D-glucose, and sugar solutions of mannose and D-galactose derived from hemicellulose. It is envisioned that any combinations of the above as well as other related sugars may be fermented using the process of the present invention.

A species of the genus was isolated from a soil sample and maintained on a potato dextrose agar plate. This specific yeast strain was biologically pure and is identified as *Brettanomyces custerii* (CBS 5512). A sample of this strain, under the Budapest Treaty as, deposited with the culture collection of American Type Culture Collection at 12301 Parklawn Drive, Rockville, Md. 20852, and is available to the public under ATCC No. 34447.

The culture medium used for fermentation in the present process can be any known culturing composition with suitable nitrogen sources, mineral supplements, vitamins, and carbon sources. These carbon sources may include hexoses (D-glucose, D-galactose, and manose) and disaccharides (D-cellobiose). Samples of the culture medium were inoculated with the *Bret-*

*tanomyces custersii* and allowed to ferment to produce ethanol. The ethanol was measured using standard gas chromatography techniques.

Oxygen tension for the fermentation process may vary widely and the oxygen tension can be either microaerophilic for batch fermentation, or the inoculated substrate may be sparged with a small amount of air in continuous fermentation techniques. Moreover, anaerobic fermentation may also be used. The technique will depend on the initial cell density, the substrate concentration, and the incubation condition of the inoculum.

The pH of the fermentation medium can range from a pH of about 3.5 to a pH of 6.0.

The temperature of the fermentation process of the present invention can also vary considerably from about 28° C. to about 42° C. However, the preferred range is about 30° C. to 39° C.

The yeast species *Brettanomyces custersii* (CBS 5512) of the present invention is capable of fermenting a wide variety of sugars as the carbon sources in the above-described culture medium.

Example of specific fermentation using the process of the invention are illustrated in the examples which follow.

---

SSF FERMENTATION

Medium:
8% Cellulose
1% Yeast Extract
2% Peptone
5 ml/L Lipids*
2 ml/L Antibiotics*
*Lipids:
Stock:
50 mg Tween-80
50 mg Ergosterol 1) Dissolve ergosterol in minimal volume of 95% ethanol (2-3 ml)
2) Mix ergosterol/ethanol solution into 50 gm Tween 80 (0.8% unesterified oleic acid)
3) Evaluate and flush with $N_2$.
   Final medium concentration = Ergosterol 5 ml/L, Oleic Acid 30 ml/L

*Antibiotics
Penicillin 10 mg/L (16,500 U)
Streptomycin 10 mg/L
Stock: (Filter Sterilize)
500 mg/Penicillin
500 mg/Streptomycin
100 ml $H_2O$

---

FOR LARGE SCALE SSF

EXAMPLE 1

Cellulose medium is added to a 6 L vessel containing 1 L of water, and the volume is brought up to about 2,500 ml in order to leave enough room for the inocula. The medium is mixed in the fermenter and a lipid stock of 5 ml/L of Egosterol and 30 ml/L of oleic acid is added, after which the mixture is autoclaved at about 120° C. for about 35 to 40 minutes. A mixture of antibiotics containing (500 mg of 10 mg/L) of penicillin and 500 mg (of 10 mg/L) of streptomycin is added and the pH is checked to insure that it is between about 4.5 to about 5.0. Thereafter, the enzyme cellulase is added and inoculum of *Brettanomyces custersii* (CBS 5512) of cell density of $2 \times 10^7$ is added in sufficient amount to bring the volume up to the 3 L mark with sterile $H_2O$. The enzyme breaks the cellulose down to glucose sugar which the yeast ferments to ethanol, and thereafter, the ethanol is separated from the fermented substrate.

FIG. 1 depicts comparative data in a simultaneous saccharification and fermentation process for the subject yeast *Brettanomyces custersii* (CBS 5512) compared to other yeast strains *T. molishiana, H. glucozyma, H. holstii, B. anomalus, S. diastaticus, S. cerevisiae* #67, *K. marxianus* and *S. cerevisiae* D5A. After only about 5 days, about 33 g/L of ethanol is produced when using the yeast strain *Brettanomyces custersii* (CBS 5512), and this is clearly superior in rate and yield when compared to the other yeast.

As is shown by FIG. 2, with the yeast *Brettanomyces custersii* (CBS 5512) screened at 37° C. with 15% cellobiose, 65 g/L of ethanol is obtained, and this yield is clearly superior to that obtained when using *B. clausenii, H. glucozyma, H. holstii* and *C. lusitaniae*.

As can be seen from the foregoing, the fermentation process of the present invention utilizing the yeast *Brettanomyces custersii* (CBS 5512) is capable of fermenting cellulose and cellobiose sugar compositions to ethanol. Most importantly, the 6 carbon sugar components of cellulose and hemicellulose, i.e., cellobiose, and glucose, are all capable of being readily fermentable to produce large yields of ethanol. Moreover, other hexoses, which are present in more minor amounts in plant biomass are also readily convertible to ethanol using the process of the present invention.

As a result of the above, this process is capable of providing large amounts of ethanol economically and from an almost unlimited supply of source material. The present invention thus provides a highly economic and useful process for fuel production. In addition, the hemicellulose components of some plant biomass do not need to be separated prior to hydrolysis and fermentation of the by-products thereof. The yeast of the present invention can be used to ferment many sugar mixtures to produce ethanol, thereby providing a much more economic process in terms of yield, the amount of time required to produce the ethanol, and the substrate materials which may be utilized.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to within the scope of the invention as defined by the claims which follow.

The embodiments of the invention in which an exclusive property of privilege is claimed are defined as follows:

What is claimed is:

1. A simultaneous, saccharification and fermentation process for producing improved yields and rates of ethanol from biomass materials, comprising:

forming a substrate from biomass materials selected from the group consisting of cellulose, hemicellulose and starch;

adding to said substrate a hydrolytic acid or a hydrolytic enzyme selected from the group consisting of cellulases, β-glucosidases, amylases and glycoamylases;

selecting and isolating a species of the yeast *Brettanomyces custersii* (CBS 5512), which-species has the ability to ferment both cellobiose and glucose to ethanol;

inoculating said substrate with said selected yeast species to obtain simultaneous saccharification and fermentation under conditions favorable for cell viability and conversion of hydrolysates to ethanol; and recovering the ethanol from said substrate.

2. The process as claimed in claim 1, wherein saccharification and fermentation of said substrate is carried out at a temperature ranging from about 28° C.–42° C.

3. The process as claimed in claim 2, wherein said temperature range comprises 30° C.–39° C.

4. The process as claimed in claim 1, wherein the pH of said inoculated substrate is maintained at about 3.5–6.0 during the saccharification and fermentation.

5. The process as claimed in claim 1, wherein said biomass is cellulose and hemicellulose, and wherein saccharification and fermentation is effected on said cellulose and hemicellulose.

6. The process as claimed in claim 5, wherein said saccharification is effected by acid hydrolysis.

7. A simultaneous, saccharification and fermentation process for producing improved rates and yields of ethanol from cellulose or starch comprising:

forming a substrate selected from the group consisting of hexoses, and dissacharides selected from sucrose, maltose, cellobiose, lactose, and mixtures thereof;

adding to said substrate a hydrolytic enzyme selected from the group consisting of cellulases, β-glucosidases, amylases and glucoamylases;

inoculating said substrate with a species of the yeast *Brettanomyces custersii* (5512) to obtain simultaneous saccharification and fermentation under conditions favorable for cell viability and conversion of hydrolysates to ethanol; and recovering the ethanol from said substrate.

8. The process as claimed in claim 7, wherein the fermentation of said inoculated substrate is carried out at a temperature ranging from about 28° C.–42° C.

9. The process as claimed in claim 7, wherein the pH of the inoculated substrate is about 3.5–6.0 during fermentation thereof.

10. The process as claimed in claim 7, wherein said hexoses are selected from the group consisting of D-glucose, mannose, D-galactose, fructose, sorbose, and mixtures thereof.

11. The process as claimed in claim 7, wherein said disaccharide is selected from the group consisting of D-cellobiose, sucrose, maltose, lactose, and mixtures thereof.

12. The process as claimed in claim 7, wherein said substrate is a disaccharide.

13. The process as claimed in claim 7, wherein said substrate comprises a mixture of at least glucose and cellobiose.

14. The process as claimed in claim 7, wherein said hexoses are hydrolysate sugars of cellulose and hemicellulose.

15. In a process for simultaneous saccharification and fermentation of aqueous sugars-containing solution to ethanol, the improvement comprising inoculating said solution with a species of the yeast *Brettanomyces custersii* (CBS 5512).

16. The improvement as claimed in claim 15, wherein fermentation is allowed to proceed until fermentation of the sugars present in said solution is substantially complete.

17. A simultaneous, saccharification and fermentation process for producing improved yields and rates of ethanol from a cellulose containing biomass material, comprising:

adding a cellulase enzyme along with yeast species *Brettanomyces custersii* (CBS 5512) to a substrate of said biomass material in a broth, such that said yeast ferments sugars formed in said broth to ethanol as said sugars are produced by cellulase hydrolysis.

18. The process of claim 7, wherein said sugars are selected from the group consisting of D-glucose, D-galactose, maltose, methyl-α-D-glucoside, sucrose, α,α-trehalose, cellobiose, and melezitose.

* * * * *